US010429323B2

(12) United States Patent
Worstell et al.

(10) Patent No.: US 10,429,323 B2
(45) Date of Patent: Oct. 1, 2019

(54) METHOD AND APPARATUS FOR PERFORMING MULTI-ENERGY (INCLUDING DUAL ENERGY) COMPUTED TOMOGRAPHY (CT) IMAGING

(71) Applicant: Photo Diagnostic Systems, Inc., Boxboro, MA (US)

(72) Inventors: William A. Worstell, Wayland, MA (US); Matthew Len Keeler, Bolton, MA (US); Olof Johnson, Ashburnham, MA (US); Bernard M. Gordon, Manchester, MA (US)

(73) Assignee: Photo Diagnostic Systems, Inc., Boxboro, MA (US)

( * ) Notice: Subject to any disclaimer, the term of this patent is extended or adjusted under 35 U.S.C. 154(b) by 314 days.

(21) Appl. No.: 15/217,742

(22) Filed: Jul. 22, 2016

(65) Prior Publication Data
US 2017/0023498 A1    Jan. 26, 2017

Related U.S. Application Data

(60) Provisional application No. 62/196,422, filed on Jul. 24, 2015.

(51) Int. Cl.
| | |
|---|---|
| G01N 23/046 | (2018.01) |
| G01N 23/087 | (2018.01) |
| A61B 6/03 | (2006.01) |
| G21K 3/00 | (2006.01) |
| A61B 6/00 | (2006.01) |

(Continued)

(52) U.S. Cl.
CPC .......... *G01N 23/046* (2013.01); *A61B 6/032* (2013.01); *A61B 6/405* (2013.01); *A61B 6/4035* (2013.01); *A61B 6/4042* (2013.01); *A61B 6/4233* (2013.01); *A61B 6/4241* (2013.01); *A61B 6/482* (2013.01); *A61B 6/52* (2013.01); *A61B 6/5205* (2013.01); *G01N 23/087* (2013.01); *G01V 5/005* (2013.01); *G01V 5/0041* (2013.01); *G21K 1/10* (2013.01); *G01N 2223/313* (2013.01); *G01N 2223/401* (2013.01); *G01N 2223/423* (2013.01)

(58) Field of Classification Search
CPC ..... A61B 6/032; A61B 6/4035; A61B 6/4042; A61B 6/405; A61B 6/4233; A61B 6/4241; A61B 6/482; A61B 6/52; A61B 6/5205; G01N 23/046; G01N 23/087; G01V 5/0041; G01V 5/005
USPC .............................. 378/5, 16, 98.9, 98.11, 57
See application file for complete search history.

(56) References Cited

U.S. PATENT DOCUMENTS

| | | | | |
|---|---|---|---|---|
| 5,115,394 | A |   | 5/1992 | Walters |
| 5,155,365 | A | * | 10/1992 | Cann ............ A61B 6/4241 250/363.02 |
| 6,028,907 | A |   | 2/2000 | Adler |

(Continued)

FOREIGN PATENT DOCUMENTS

DE    10 2011 005 161    10/2016

OTHER PUBLICATIONS

Brennan, Linear Diversity Combining Techniques, Proceedings of the IEEE, Feb. 2003, vol. 91, No. 2, pp. 331-356.

(Continued)

*Primary Examiner* — Allen C. Ho
(74) *Attorney, Agent, or Firm* — Pandiscio & Pandiscio

(57) ABSTRACT

An improved dual energy CT imaging system for providing improved imaging and improved material identification.

21 Claims, 10 Drawing Sheets

(51) Int. Cl.
*G21K 1/10* (2006.01)
*G01V 5/00* (2006.01)

(56) References Cited

U.S. PATENT DOCUMENTS

| | | | |
|---|---|---|---|
| 6,122,344 A | 9/2000 | Beevor | |
| 6,904,118 B2 | 6/2005 | Wu et al. | |
| 6,950,492 B2* | 9/2005 | Besson | A61B 6/032 378/16 |
| 6,950,493 B2* | 9/2005 | Besson | A61B 6/032 378/16 |
| 6,973,158 B2* | 12/2005 | Besson | A61B 6/032 378/16 |
| 6,987,833 B2 | 1/2006 | Du et al. | |
| 6,997,610 B2 | 2/2006 | Heismann | |
| 7,027,561 B2 | 4/2006 | Francke et al. | |
| 7,158,611 B2 | 1/2007 | Heismann et al. | |
| 7,175,347 B2* | 2/2007 | Tybinkowski | A61B 6/032 378/198 |
| 7,190,757 B2 | 3/2007 | Ying et al. | |
| 7,215,732 B2* | 5/2007 | Yin | G06T 11/005 378/5 |
| 7,217,927 B2 | 5/2007 | Worstell | |
| 7,272,429 B2 | 9/2007 | Walker | |
| 7,298,812 B2 | 11/2007 | Tkaczyk et al. | |
| 7,315,604 B2* | 1/2008 | Raupach | A61B 6/032 378/5 |
| 7,396,160 B2* | 7/2008 | Tybinkowski | A61B 6/032 378/147 |
| 7,397,895 B2* | 7/2008 | Bailey | A61B 6/032 378/102 |
| 7,420,675 B2 | 9/2008 | Giakos | |
| 7,438,471 B2* | 10/2008 | Tybinkowski | A61B 6/032 378/197 |
| 7,453,974 B2* | 11/2008 | Van Steven-Daal | A61B 6/032 378/207 |
| 7,551,708 B2* | 6/2009 | Basu | G01N 23/046 378/5 |
| 7,568,836 B2* | 8/2009 | Bailey | A61B 6/032 378/198 |
| 7,583,779 B2* | 9/2009 | Tkaczyk | A61B 6/032 378/4 |
| 7,627,080 B2 | 12/2009 | Proksa | |
| 7,688,936 B2* | 3/2010 | Toth | A61B 6/032 378/101 |
| 7,697,657 B2* | 4/2010 | Walter | A61B 6/4241 378/4 |
| 7,724,865 B2* | 5/2010 | Wu | A61B 6/032 378/4 |
| 7,742,564 B2* | 6/2010 | Parham | G01N 23/046 378/70 |
| 7,773,725 B2* | 8/2010 | Gordon, III | G01N 23/18 378/53 |
| 7,778,380 B2* | 8/2010 | Altman | A61B 6/482 378/4 |
| 7,778,454 B2 | 8/2010 | Grasruck et al. | |
| 7,826,587 B1* | 11/2010 | Langan | A61B 6/032 378/16 |
| 7,889,834 B2 | 2/2011 | Heismann | |
| 8,055,039 B2* | 11/2011 | Wu | G06T 5/002 382/128 |
| 8,086,012 B2* | 12/2011 | Toth | A61B 5/411 378/4 |
| 8,111,803 B2* | 2/2012 | Edic | A61B 6/4035 378/146 |
| 8,155,422 B2* | 4/2012 | Ziegler | G01T 1/2985 378/4 |
| 8,160,206 B2* | 4/2012 | Wu | A61B 6/032 378/4 |
| 8,165,264 B2 | 4/2012 | Zou | |
| 8,199,874 B2* | 6/2012 | Toth | A61B 6/032 378/16 |
| 8,199,875 B2* | 6/2012 | Chandra | A61B 6/032 378/16 |
| 8,218,837 B2* | 7/2012 | Wu | A61B 6/032 382/128 |
| 8,229,060 B2* | 7/2012 | Proksa | A61B 6/032 378/5 |
| 8,260,023 B2* | 9/2012 | Thomsen | A61B 6/032 382/128 |
| 8,294,717 B2* | 10/2012 | Zamyatin | G06K 9/342 345/440 |
| 8,311,181 B2* | 11/2012 | Thomsen | G06T 11/006 378/5 |
| 8,311,182 B2* | 11/2012 | Chandra | A61B 6/03 378/5 |
| 8,315,352 B2 | 11/2012 | Wu et al. | |
| 8,494,244 B2* | 7/2013 | Dutta | A61B 6/032 382/131 |
| 8,588,494 B2* | 11/2013 | De Man | G06T 11/008 378/18 |
| 8,705,822 B2* | 4/2014 | Yu | G06T 11/006 378/5 |
| 8,787,519 B2* | 7/2014 | Fan | A61B 6/032 378/5 |
| 8,855,385 B2* | 10/2014 | Kriston | A61B 6/12 128/922 |
| 9,036,879 B2* | 5/2015 | Mendonca | A61B 6/032 378/4 |
| 9,036,886 B2 | 5/2015 | Hsieh et al. | |
| 9,074,986 B2* | 7/2015 | Pal | G01N 23/046 |
| 9,135,728 B2* | 9/2015 | Fan | A61B 6/06 |
| 9,208,585 B2* | 12/2015 | Leng | A61B 6/032 |
| 9,208,918 B2* | 12/2015 | Tybinkowski | G21K 1/02 |
| 9,211,066 B2* | 12/2015 | Johnson | A61B 6/12 |
| 9,269,168 B2* | 2/2016 | Inglese | A61B 6/4241 |
| 9,271,688 B2* | 3/2016 | Das | A61B 6/481 |
| 9,498,179 B1* | 11/2016 | Sen Sharma | A61B 6/5258 |
| 9,532,759 B2* | 1/2017 | Taguchi | A61B 6/032 |
| 9,585,626 B2* | 3/2017 | Gao | A61B 6/032 |
| 9,610,055 B2* | 4/2017 | Taguchi | A61B 6/5205 |
| 9,713,452 B2* | 7/2017 | Narayanan | A61B 6/032 |
| 9,747,704 B2* | 8/2017 | Taguchi | G06T 11/005 |
| 9,861,324 B2* | 1/2018 | Wang | A61B 6/482 |
| 9,913,622 B2* | 3/2018 | Ida | A61B 6/5205 |
| 9,984,476 B2* | 5/2018 | Hsieh | G06T 11/003 |
| 2006/0203956 A1 | 9/2006 | Raupach | |
| 2007/0078336 A1 | 4/2007 | Toth | |
| 2009/0052621 A1 | 2/2009 | Walter et al. | |
| 2012/0039440 A1 | 2/2012 | Fan et al. | |
| 2014/0187932 A1 | 7/2014 | Li et al. | |
| 2014/0270440 A1 | 9/2014 | Inglese et al. | |
| 2014/0321603 A1 | 10/2014 | Taguchi et al. | |

OTHER PUBLICATIONS

Genant et al., Quantitative Bone Mineral Analysis Using Dual Energy Computed Tomography, Investigative Radiology, Nov.-Dec. 1977, vol. 12, No. 6, pp. 545-551.

Goodsitt et al., Quantitative Computed Tomography Scanning for Measurement of Bone and Bone Marrow Fat Content, Investigative Radiology, Oct. 1987, vol. 22, No. 10, pp. 799-810.

Jennings et al., Optimal x-ray spectra for screen-film mammography, Med. Phys., Sep./Oct. 1981, vol. 8, No. 5, pp. 629-639.

Maaß0 et al., Exact dual energy material decomposition from inconsistent rays (MDIR), Med. Phys., Feb. 2011, vol. 38, No. 2, pp. 691-700.

Mouton et al., A Novel intensity Limiting Approach to Metal Artefact Reduction in 3D CT Baggage Imagery, Proc. International Conference on Image Processing, IEEE, 2012, pp. 2057-2060.

Rietzel et al., Deformable registration of 4D computed tomography data, Med. Phys., Nov. 2006, vol. 33, No. 11, pp. 4423-4430.

Vetter et al., Correction for scattered radiation and other background signals in dual-energy computed tomography material thickness measurements, Medical Physics, vol. 15, No. 5, 726-731, Sep./Oct. 1988.

(56) References Cited

OTHER PUBLICATIONS

Beaulieu N. C., Introduction to "Linear Diversity Combining Techniques", Proceedings of the IEEE, Feb. 2003, vol. 91, No. 2, pp. 328-330.
Glover G.H. et al., An algorithm for the reduction of metal clip artifacts in CT reconstructions, Med. Phys., Nov./Dec. 1981, vol. 8, No. 6, pp. 799-807.
Goodsitt M.M. et al., Accuracies of the synthesized monochromatic CT numbers and effective atomic numbers obtained with a rapid kVp switching dual energy CT scanner, Med. Phys., Apr. 2011, vol. 38, No. 4, pp. 2222-2232.
Jeong K.Y. et al., Reduction of artifacts due to multiple metallic objects in computed tomography, Proc. SPIE, 2009, vol. 7258.
Kalender W.A. et al., Reduction of CT Artifacts Caused by Metallic Implants, Radiology, Aug. 1987, vol. 164, pp. 576-577.
Kuchenbecker S. et al., Dual energy CT: How well can pseudo-monochromatic imaging reduce metal artifacts?, Med. Phys., Feb. 2015, vol. 42, No. 2, pp. 1023-1036.
Mouton A. et al., An Experimental Survey of Metal Artefact Reduction in Computed Tomography, Journal of X-Ray Science and Technology. 2013, vol. 21, No. 2, pp. 193-226.
Riedel M., An Introduction to Dual Energy Computed Tomography, University of Texas Health Science Center at San Antonio, 2010.
Seco J. et al., Assessing the effect of electron density in photon dose calculations, Med. Phys., Feb. 2006, vol. 33, No. 2, pp. 540-552.
Song L. et al., High-speed dynamic 3D photoacoustic imaging of sentinel lymph node in a murine model using an ultrasound array, Med. Phys., Aug. 2009, vol. 36, No. 8, pp. 3724-3729.
Worstell W. et al., Diversity Combining Signal Processing and NEC in List-Mode PET, IEEE, 2004, vol. 6, pp. 3814-3818.
Xia T. et al., Noise and Bias Properties of Monoenergetic Images from DECT used for Attenuation Correction with PET/CT and Spect/CT, Proc. SPIE, May 2010, pp. 762225-762228.
Ying Z, et al,, Dual energy computed tomography for explosive detection, Journal of X-Ray Science and Technology, 2006, vol. 14, pp. 235-256.
Yu L. et al., Dual-Energy CT-Based Monochromatic Imaging, AJR, Nov. 2012, vol. 199, pp. S9-S15.
Johnson et al., "Material differentiation by dual energy CT: initial experience", Eur. Radiol., vol. 17, No. 6, 2006, pp. 1510-1517.
Lehmann et al., "Generalized image combinations in dual KVP digital radiography", Med. Phys., vol. 8, No. 5, 1981, pp. 659-667.
Maaß et al., "Image-based dual energy CT using optimized precorrection functions: A practical new approach of material decomposition in image domain", Med. Phys., vol. 36, No. 8, 2009.
Szczykutowicz et al., "A simple image based method for obtaining electron density and atomic number in dual energy CT", Proc. SPIE, vol. 7961, 2011.
Wang et al., "A Review of Dual Energy CT: Principles, Applications, and Future Outlook", CT Theories and Applications, vol. 21, No. 3, Sep. 2012, pp. 367-386.

\* cited by examiner

| Raw Data | |
|---|---|
| Filtered Detector Signal (polyenergetic higher energy) | Unfiltered Detector Signal (polyenergetic lower energy) |
| 600 | 1000 |

| Multiplier | |
|---|---|
| Raitio of Filtered/Unfiltered | |
| 0.6 | |
| Lookup Ratio Index (ratio x 100) | |
| 60 | |
| Lookup Signal Index (filtered signal) | Lookup Signal Index (unfiltered signal) |
| 600 | 1000 |
| Multiplier For Filtered Data | Multiplier for Unfiltered Data |
| 2 | 1.2 |

| Monochromatic Data | |
|---|---|
| Converted Filtered Detector Signal = 2 x 600 | Converted Unfiltered Detector Signal = 1.2 x 1000 |
| 1200 | 1200 |

FIG. 10

METHOD AND APPARATUS FOR PERFORMING MULTI-ENERGY (INCLUDING DUAL ENERGY) COMPUTED TOMOGRAPHY (CT) IMAGING

REFERENCE TO PENDING PRIOR PATENT APPLICATION

This patent application claims benefit of U.S. Provisional Patent Application Ser. No. 62/196,422, filed Jul. 24, 2015 by Photo Diagnostic Systems, Inc. and William A. Worstell et al. for METHOD AND APPARATUS FOR PERFORMING DUAL ENERGY COMPUTED TOMOGRAPHY (CT) IMAGING, which patent application is hereby incorporated herein by reference.

FIELD OF THE INVENTION

This invention relates to imaging systems in general, and more particularly to computed tomography (CT) imaging systems.

BACKGROUND OF THE INVENTION

In many situations it can be desirable to image the interior of an object. By way of example but not limitation, in the medical field, it can be desirable to image the interior of a patient's body so as to allow viewing of internal structures without physically penetrating the skin. By way of further example but not limitation, in the security field, it can be desirable to image the interior of a container (e.g., a suitcase, a package, etc.) so as to allow viewing of internal structures without physically opening the container.

Computed Tomography (CT)

Computed Tomography (CT) has emerged as a key imaging modality in the medical and security fields, among others. CT imaging systems generally operate by directing X-rays into an object (e.g., a body or a container) from a variety of positions, detecting the X-rays passing through the object, and then processing the detected X-rays so as to build a three-dimensional (3D) data set, and a 3D computer model, of the interior of the object (e.g., the patient's anatomy or the contents of the container). The 3D data set and 3D computer model can then be visualized so as to provide images (e.g., slice images, 3D computer images, etc.) of the interior of the object (e.g., the patient's anatomy or the contents of the container).

By way of example but not limitation, and looking now at FIGS. 1 and 2, there is shown an exemplary prior art CT imaging system 5. CT imaging system 5 generally comprises a torus 10 which is supported by a base 15. A center opening 20 is formed in torus 10. Center opening 20 receives the object (e.g., the body or the container) which is to be scanned by CT imaging system 5.

Looking next at FIG. 3, torus 10 generally comprises a fixed gantry 25, a rotating disc 30, an X-ray tube assembly 35 and an X-ray detector assembly 40. More particularly, fixed gantry 25 is disposed concentrically about center opening 20. Rotating disc 30 is rotatably mounted to fixed gantry 25. X-ray tube assembly 35 and X-ray detector assembly 40 are mounted to rotating disc 30 in diametrically-opposing relation, such that an X-ray beam 45 (generated by X-ray tube assembly 35 and detected by X-ray detector assembly 40) is passed through the object (e.g., the body or the container) disposed in center opening 20. Inasmuch as X-ray tube assembly 35 and X-ray detector assembly 40 are mounted on rotating disc 30 so that they are rotated concentrically about center opening 20, X-ray beam 45 will be passed through the object (e.g., the body or the container) along a full range of radial positions, so as to enable CT imaging system 5 to create a "slice" image of the object penetrated by the X-ray beam. Furthermore, by moving the object (e.g., the body or the container) and/or CT imaging system 5 relative to one another during scanning, a series of slice images can be acquired, and thereafter appropriately processed, so as to create a 3D data set of the scanned object and a 3D computer model of the scanned object.

In practice, it is now common to effect helical scanning of the object so as to generate a 3D data set of the scanned object, which can then be processed to build a 3D computer model of the scanned object. The 3D data set and/or 3D computer model can then be visualized so as to provide images (e.g., slice images, 3D computer images, etc.) of the interior of the object (e.g., the patient's anatomy or the contents of the container).

Beam Hardening

In practice, X-ray tube assembly 35 is typically a polychromatic X-ray source, i.e., X-ray tube assembly 35 typically comprises an X-ray tube of the sort which emits X-rays with a range of different energies. However, as the X-ray beam from a polychromatic X-ray source passes through the object which is being scanned, low energy X-ray photons are generally attenuated more easily than high energy X-ray photons. Thus, the X-ray beam from a polychromatic X-ray source preferentially loses the lower-energy parts of its spectrum as it passes through the object. This is a particular problem with high atomic number materials such as bone and metals which can heavily attenuate the lower-energy parts of the X-ray beam, and can (among other things) produce image artifacts between two high attenuation materials (e.g., between two materials which have high atomic numbers). This phenomenon is sometimes referred to as "beam hardening". Various algorithms have been developed in an effort to correct for beam hardening, but such algorithms generally suffer from the fact that they require certain assumptions to be made (e.g., that the polychromatic X-ray source has a fixed spectrum which does not change as the X-ray tube heats up, that the X-ray absorption spectrum has an idealized shape, etc.).

Dual Energy CT

X-ray attenuation is generally caused by (i) the scattering of radiation by the object which is being scanned, and/or (ii) the absorption of radiation by the object which is being scanned. The mechanisms primarily responsible for these two effects are Compton scatter and photoabsorption. Compton scatter and photoabsorption vary according to (a) the energy of the photons in the X-rays, and (b) the composition of the object which is being scanned. For this reason, it has been recognized that measurements taken at two different X-ray energies (i.e., "dual energy") can be used to distinguish between different materials in the object which is being scanned. These two different measured X-ray energies are not necessarily restricted to monochromatic measurements, and in practice the two measurements are taken over broad ranges of low and high energies (i.e., a low-energy polychromatic measurement is used as one of the X-ray energies of the dual energy scan, and a high-energy polychromatic measurement is used as the other of the X-ray energies of the dual energy scan).

Several different approaches can be used to generate measurements of two different X-ray energy ranges.

First, two different X-ray spectra can be applied to the object which is being scanned, and an unfiltered detector can be used to detect the differences in attenuation by the object which is being scanned. Accordingly, with some dual energy CT imaging systems, the system is provided with a single X-ray tube with rapid switching between two different voltages, and an unfiltered detector is used to detect the differences in attenuation by the object which is being scanned with two different X-ray voltages. However, this approach suffers from relatively high cost, since it requires that the single X-ray tube be driven by two different voltages, which generally requires the provision of either two high-voltage power supplies or a single high-speed switching power supply. With other dual energy CT imaging systems, the system is provided with two X-ray tubes driven at different voltages (whereby to apply two different X-ray spectra to the object which is being scanned), and an unfiltered detector is used to detect the differences in attenuation by the object which is being scanned by the two different X-ray tubes/two different X-ray tube voltages. However, this approach also suffers from relatively high cost, since it requires the provision of two X-ray tubes.

Second, it has also been recognized that a single X-ray spectra can be applied to the object which is being scanned, and then a dual-filter detector (i.e., a detector having two different X-ray spectrum filters) can be used to obtain measurements over two different X-ray energy ranges (e.g., a "high" X-ray energy band and a "low" X-ray energy band), whereby to detect the differences in attenuation by the object which is being scanned. Accordingly, with some dual energy CT imaging systems, the system is provided with a single X-ray tube driven by a single voltage, and a dual-filter detector is used to obtain measurements over two different X-ray energy ranges, i.e., one filter is configured to maximize the detection of higher energy photons and one filter is configured to maximize the detection of lower energy photons. However, this approach suffers from relatively inefficient use of the available photons, because each filter must be something of a compromise in determining what fraction of the photons of the "undesired" spectrum must be allowed to pass in order to get some portion of the photons of the "desired" spectrum. Stated another way, the two filters used in the dual-filter detector cannot cut off at an infinite rate, therefore, the design of each filter must be something of a compromise.

Again, where the X-ray source is a polychromatic X-ray source (i.e., the X-ray tube assembly emits X-rays with a range of different energies), issues arise due to beam hardening (i.e., the preferential attenuation of low energy X-ray photons by the object being scanned). This can create issues in material identification. Again, various algorithms have been developed in an effort to correct for beam hardening, but such algorithms generally suffer from the fact that they require certain assumptions to be made (e.g., that the polychromatic X-ray source has a fixed spectrum which does not change as the X-ray tube heats up, that the X-ray absorption spectrum has an idealized shape, etc.).

Thus there is a need for an improved multi-energy (including dual energy) CT imaging system providing improved imaging (e.g., images free of beam hardening artifacts or approximations) and improved material identification.

SUMMARY OF THE INVENTION

These and other objects of the present invention are addressed by the provision and use of an improved multi-energy (including dual energy) CT imaging system providing improved imaging (e.g., images free of beam hardening artifacts or approximations) and improved material identification.

In one preferred form of the invention, there is provided a novel approach for performing dual energy CT imaging.

First, the object is scanned using a CT imaging system comprising (i) an X-ray tube assembly comprising a single X-ray tube driven at a single voltage and producing a polychromatic X-ray beam, and (ii) an X-ray detector assembly wherein each detector is capable of measuring two different X-ray energy ranges, i.e., a "high energy measurement" and a "low energy measurement". This may be done using conventional "dual-filter" detectors or using a novel "single-filter" detector as described herein. In either case, such scanning produces two polyenergetic signals, $g_{HIGH}$ ("high energy") and $g_{LOW}$ ("low energy"), for each rotational position of the X-ray tube assembly/X-ray detector assembly about the object which is being scanned, i.e., for each "line of response". In general, additional filters (or their functional equivalent) may be used to obtain additional polyenergetic signals which can be used to further supplement the available spectral information, e.g., appropriate filtering may be provided to generate three or more polyenergetic signals for enabling multi-energy CT.

Next, for each line of response, the ratio $g_{HIGH}/g_{LOW}$ (or "R") is computed.

R and g (i.e., $g_{HIGH}$ or $g_{LOW}$) are then used as the indices for an appropriate lookup table to obtain multiplicative factors ("A" or "B", respectively) to transform the polyenergetic data g (i.e., $g_{HIGH}$ or $g_{LOW}$, respectively) into the predicted signal for a purely monochromatic system of any monoenergy. The monoenergetic sinogram ($G_{ENERGY}$) comprises the collection of monoenergetic signals for any single energy (subscript "$_{ENERGY}$") at every line of response including the lines of response associated with both highly filtered ($g_{HIGH}$) and lesser filtered or unfiltered ($g_{LOW}$) detectors. Note that the function R need not be the specific ratio $g_{HIGH}/g_{LOW}$, or any other ratio for that matter, but may be any function which is sensitive to the differential response of the two (or more) different kinds of detector channels $g_{HIGH}$ and $g_{LOW}$.

A lookup table (comprising the appropriate multiplicative factors "$A_{ENERGY}$" and "$B_{ENERGY}$") can be generated to produce a corresponding monochromatic sinogram $G_{ENERGY}$, and from there, a corresponding image for any single monoenergy (subscript "$_{ENERGY}$"). By way of example but not limitation, a lookup table (comprising the appropriate multiplicative factors "$A_{160}$" and "$B_{160}$") can be generated to produce a corresponding monochromatic sinogram $G_{160}$ (i.e., a corresponding monochromatic sinogram at monoenergy 160 kev), and from there, a corresponding image $I_{160}$ for that monoenergy (i.e., a corresponding image for that monoenergy 160 kev). By way of further example but not limitation, a lookup table (comprising the appropriate multiplicative factors "$A_{40}$" and "$B_{40}$") can be generated to produce a corresponding monochromatic sinogram $G_{40}$ (i.e., a corresponding monochromatic sinogram at monoenergy 40 kev), and from there, a corresponding image $I_{40}$ for that monoenergy (i.e., a corresponding image for that monoenergy 40 kev).

Significantly, these "synthetic" monoenergetic images (e.g., $I_{160}$, $I_{40}$, etc.) are free of beam hardening artifacts.

Furthermore, material composition can be obtained by a suitable function operating on one or more monoenergetic images (e.g., $I_{160}$, $I_{40}$, etc.).

For example, a monoenergetic ratio image $I_R$ can be produced and used to determine (i) the effective atomic number ($Z_{eff}$) for each voxel in the fused image, and (ii) the electron density (Rho) for each voxel in the fused image, so that the material composition of the object can be determined. By way of example but not limitation, $I_R$ may be $I_{160}/I_{40}$.

In general, the signals $g_x$ associated with the differently filtered detectors, in conjunction with the function R, can be transformed to an equivalent signal assuming a monoenergetic X-ray source. This transformation may be a simple mathematical function, but in most instances a lookup table is the preferred embodiment because of the computational savings available by using a lookup table. In addition, the transformation from a polyenergetic signal to an equivalent monoenergetic signal may be empirically derived, in which case a table-based implementation is preferred. This method of correcting for beam hardening is, in principle, exact, and does not suffer from the approximations present in other methodologies.

The monoenergetic images, being free of beam-hardening, can be used to characterize different aspects of the materials being scanned. In one implementation, a large number of monoenergetic images can be assembled to produce a virtual "X-ray spectrometer" where each voxel of the assembled image has the full absorption spectrum. In the opposite extreme, it may be useful to simply predict the absorptive properties of materials at a single monoenergy. For example, this method can be used to predict the absorption of high energy gamma rays used in nuclear imaging (Single Photon Emission Computed Tomography "SPECT" scanning uses the radioactive element Technetium-99, which emits monochromatic 140 kev radiation). In the preferred embodiment, two monoenergetic images (e.g., $I_{160}$ and $I_{40}$) are transformed into a monoenergetic ratio image $I_R$ whose values are proportional to the effective atomic number of the scanned material. Other material or physical properties can be derived from monochromatic images (e.g., $I_{160}$ and $I_{40}$) such as electron density (Rho) or degree of Compton scattering.

In one preferred form of the invention, there is provided a multi-energy computed tomography (CT) imaging system for providing an image of an object, the system comprising:
    a polychromatic X-ray source;
    a detector for detecting X-rays from the polychromatic X-ray source after the X-rays have passed through an object and for providing a first set of polychromatic energy measurements relating to a first polychromatic X-ray spectrum passed through the object and for providing a second set of polychromatic energy measurements relating to a second polychromatic X-ray spectrum passed through the object; and
    a processor configured to:
        (i) transform at least one of the first set of polychromatic energy measurements and the second set of polychromatic energy measurement into a corresponding first monochromatic data set associated with X-rays at a selected first monochromatic energy level and into a corresponding second monochromatic data set associated with X-rays at a selected second monochromatic energy level;
        (ii) transform the first monochromatic data set into a first monochromatic image and transform the second monochromatic data set into a second monochromatic image; and
        (iii) use at least one of the first monochromatic image and the second monochromatic image to perform at least one of (a) provide an image free from beam hardening artifacts, and (b) provide identification of material properties within the object.

In another preferred form of the invention, there is provided a method for providing an image of an object free from beam hardening artifacts and/or providing identification of material properties of the object, the method comprising:
    providing a first set of polychromatic energy measurements relating to a first polychromatic X-ray spectrum passed through the object and providing a second set of polychromatic energy measurements relating to a second polychromatic X-ray spectrum passed through the object;
    transforming at least one of the first set of polychromatic energy measurements and the second set of polychromatic energy measurement into a corresponding first monochromatic data set associated with X-rays at a selected first monochromatic energy level and into a corresponding second monochromatic data set associated with X-rays at a selected second monochromatic energy level;
    transforming the first monochromatic data set into a first monochromatic image and transforming the second monochromatic data set into a second monochromatic image; and
    using at least one of the first monochromatic image and the second monochromatic image to provide at least one of (a) an image free from beam hardening artifacts, and (b) identification of material properties within the object.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein:

FIG. 10 is a table showing how raw polychromatic data may be transformed into equivalent monochromatic data.

DETAILED DESCRIPTION OF THE PREFERRED EMBODIMENTS

In accordance with the present invention, there is provided a novel multi-energy (including dual energy) CT imaging system providing improved imaging (e.g., images free of beam hardening artifacts or approximations) and improved material identification.

Apparatus for Performing Dual Energy

Computed Tomography (CT) Imaging

Figure 1:
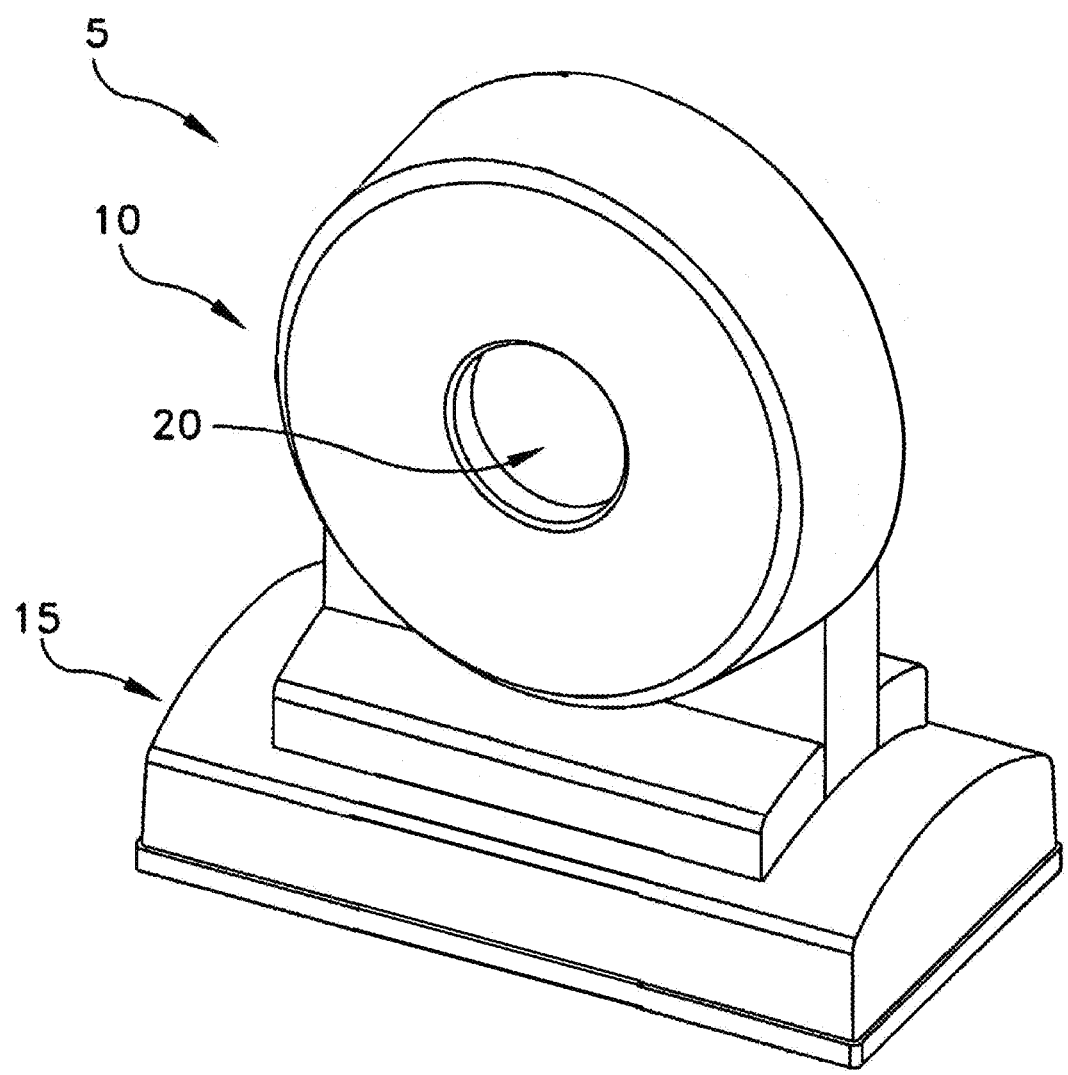
FIGS. 1 and 2 are schematic views showing the exterior of an exemplary prior art CT imaging system.
Figure 2:
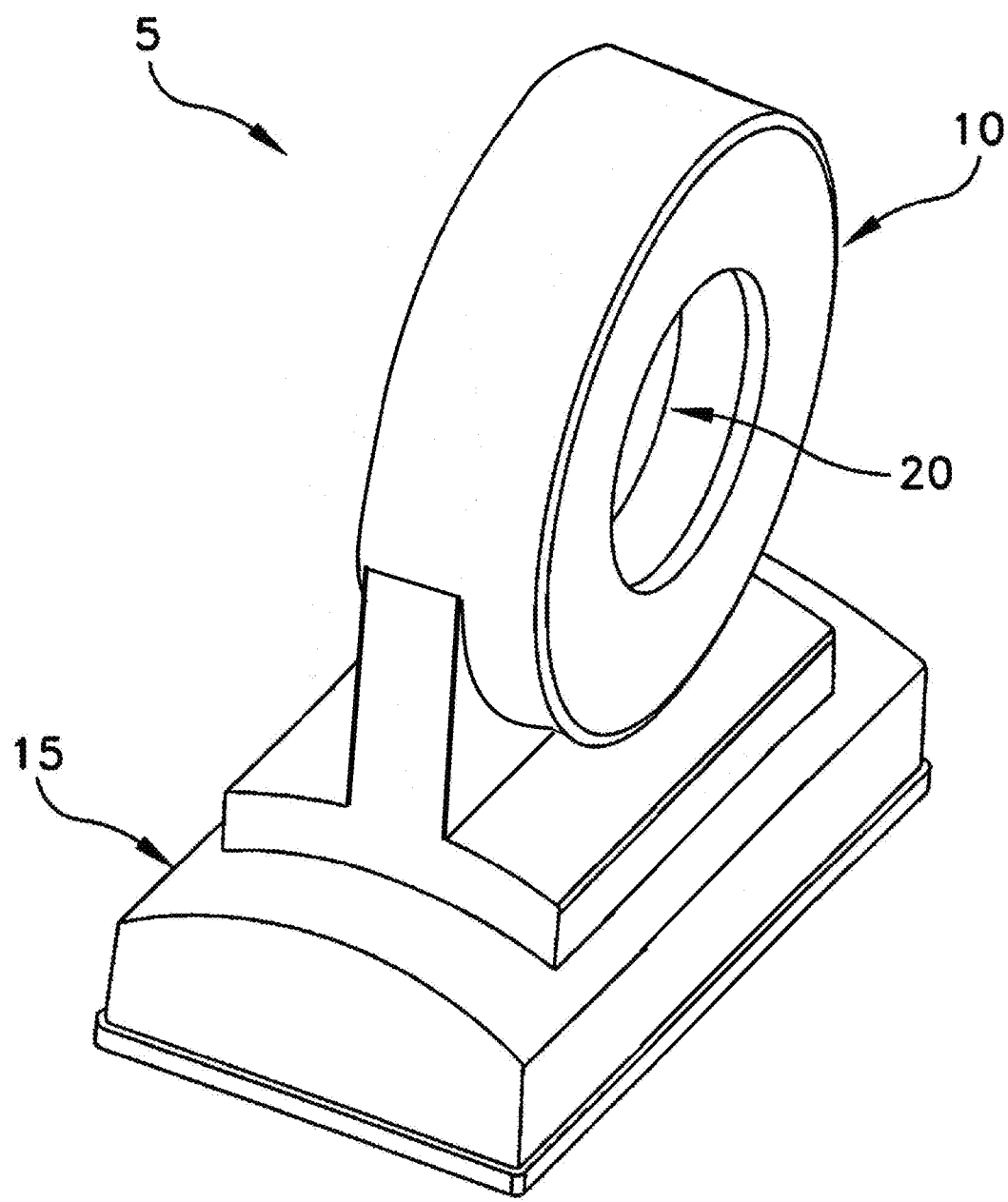
Figure 3:
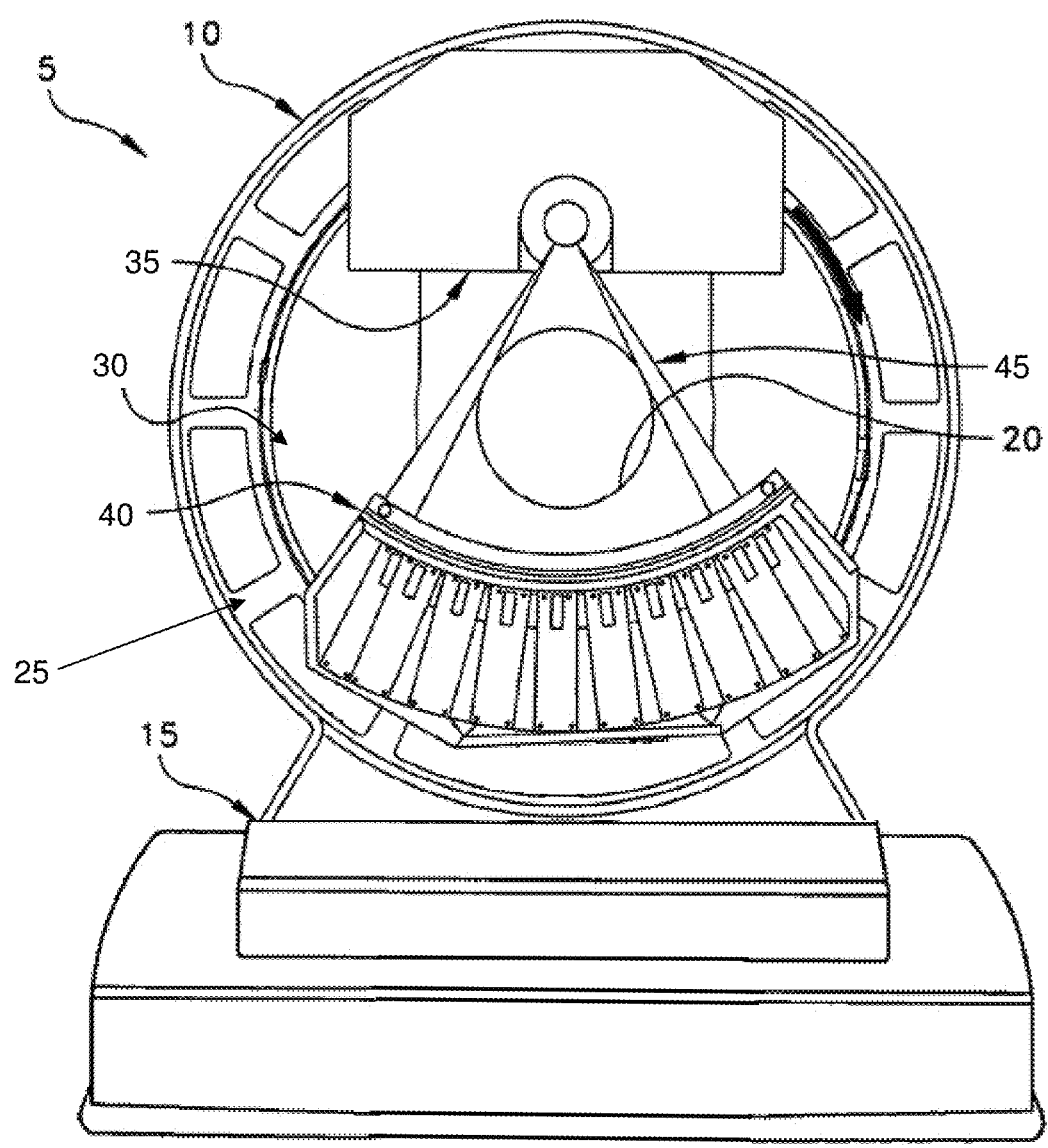
FIG. 3 is a schematic view showing various components in the torus of the exemplary prior art CT imaging system shown in FIGS. 1 and 2.
Figure 4:
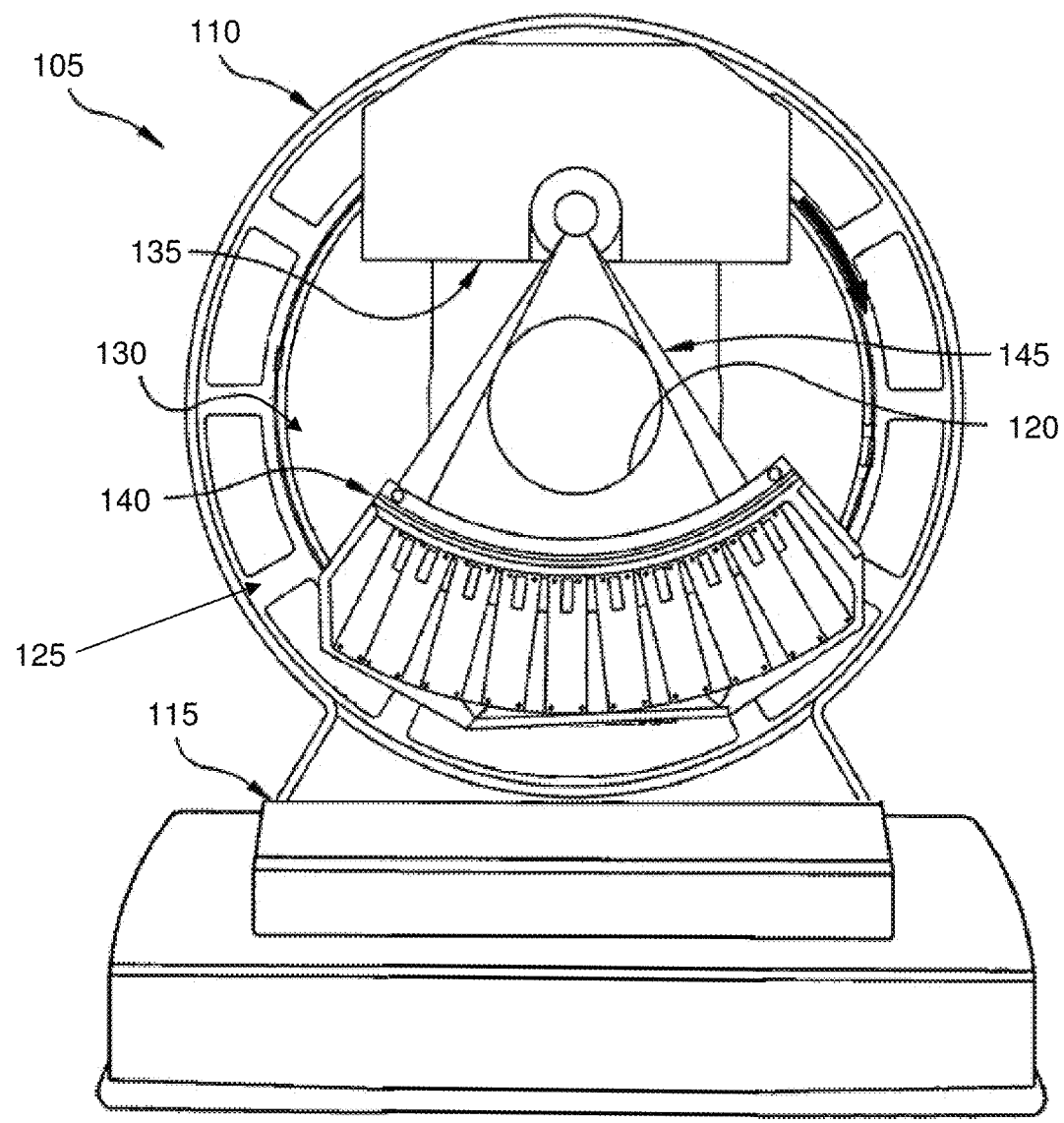
FIG. 4 is a schematic view showing components in the torus of a novel multi-energy (including dual energy) CT imaging system formed in accordance with the present invention.

In accordance with the present invention, and looking now at FIG. 4, there is provided a novel multi-energy (including dual energy) CT imaging system 105. Multi-energy (including dual energy) CT imaging system 105 is substantially the same as the exemplary prior art CT imaging system 5 previously discussed, except as will hereinafter be discussed.

More particularly, in the preferred form of the present invention, multi-energy (including dual energy) CT imaging system 105 generally comprises a torus 110 which is supported by a base 115. A center opening 120 is formed in torus 110. Center opening 120 receives the object (e.g., the body or the container) which is to be scanned by multi-energy (including dual energy) CT imaging system 105.

Still looking now at FIG. 4, torus 110 generally comprises a fixed gantry 125, a rotating disc 130, an X-ray tube assembly 135 and an X-ray detector assembly 140. More particularly, fixed gantry 125 is disposed concentrically about center opening 120. Rotating disc 130 is rotatably mounted to fixed gantry 125. X-ray tube assembly 135 and X-ray detector assembly 140 are mounted to rotating disc 130 in diametrically-opposing relation, such that an X-ray beam 145 (generated by X-ray tube assembly 135 and detected by X-ray detector assembly 140) is passed through the object (e.g., the body or the container) disposed in center opening 120.

In one preferred form of the invention, X-ray tube assembly 135 comprises a polychromatic X-ray tube assembly, i.e., X-ray tube assembly 135 emits X-rays with a range of different energies. In one preferred form of the invention, X-ray tube assembly 135 comprises a single X-ray tube which is driven by a single voltage.

Inasmuch as X-ray tube assembly 135 comprises a single polychromatic X-ray tube driven by a single voltage, in order to allow the imaging system to be used for multi-energy (including dual energy) CT imaging, it is necessary for X-ray detector assembly 140 to provide, for each of its detectors, measurements at two or more different X-ray energy ranges, e.g., a "high energy measurement" which maximizes the detection of higher energy photons and a "low energy measurement" which maximizes the detection of lower energy photons, with or without additional energy measurements.

For clarity of description, multi-energy (including dual energy) CT imaging system 105 will generally hereinafter be discussed in the context of a dual energy CT imaging system, however, it should be appreciated that the CT imaging system may utilize three or more energy measurements without departing from the scope of the present invention.

Figure 5:
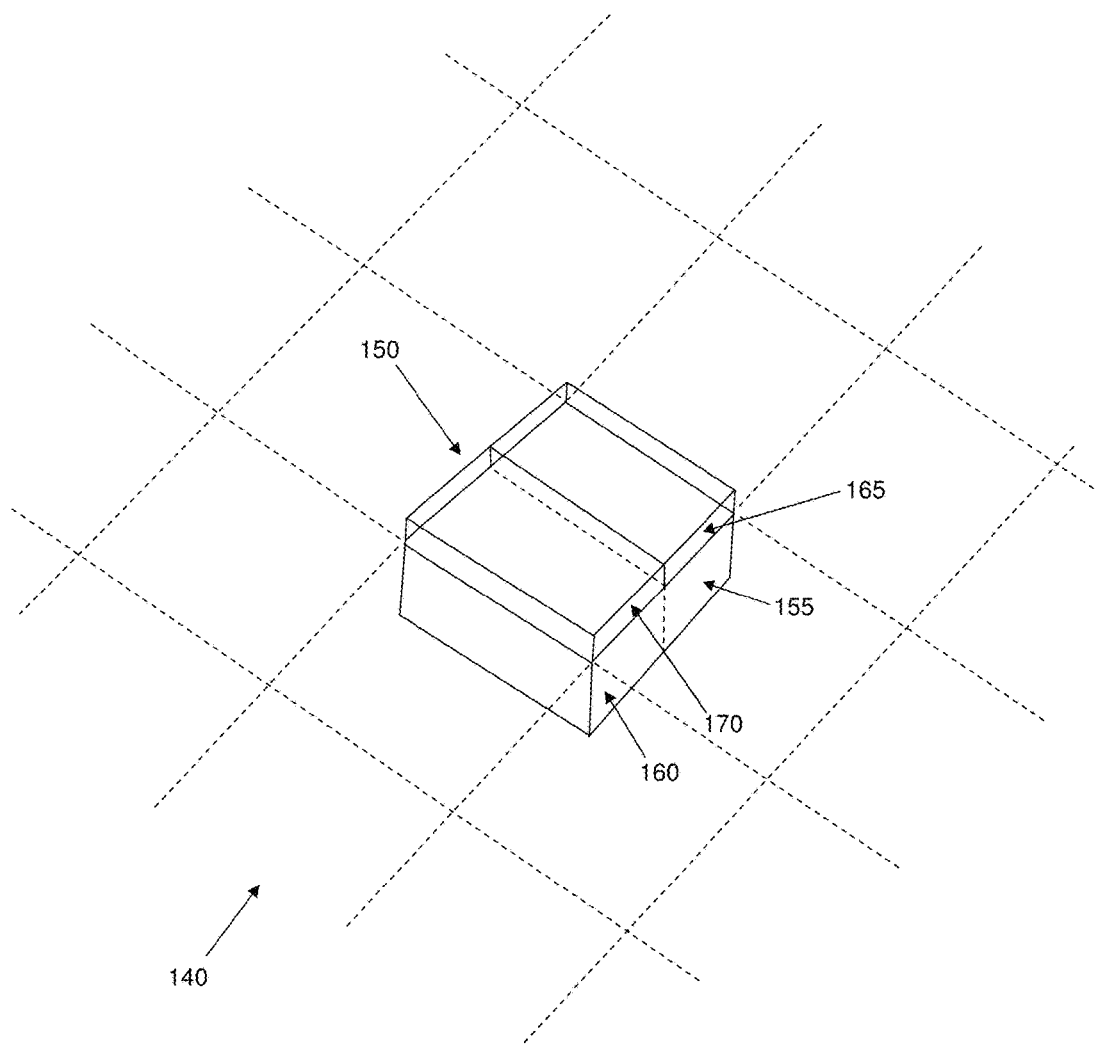
FIG. 5 is a schematic view of a dual-filter detector which may be utilized in the X-ray detector assembly of the novel multi-energy (including dual energy) CT imaging system shown in FIG. 4.

If desired, this may be accomplished in the manner of the prior art, i.e., by providing a dual-filter detector such as the dual-filter detector shown in FIG. 5. More particularly, in this form of the invention, each detector 150 (FIG. 5) of X-ray detector assembly 140 is provided with two separate detection regions 155, 160, with detection region 155 being provided with a first filter 165 which is configured to maximize the detection of higher energy photons (whereby to provide the "high energy measurement" used for dual energy CT scanning), and with detection region 160 being provided with a second, different filter 170 which is configured to maximize the detection of lower energy photons (whereby to provide the "low energy measurement" used for dual energy CT scanning). However, this prior art approach has the drawback of increased cost and lower photon yield, particularly with respect to the "low energy measurement" since the "low energy measurement" is restricted to low energy photons and such low energy photons are more heavily attenuated as they encounter the object being scanned, thereby yielding lower photon yields.

For this reason, the present invention provides an improved approach for providing, for each of its detectors, measurements at two different X-ray energy ranges (i.e., a "high energy measurement" and a "low energy measurement") in order to enable dual energy CT scanning.

Figure 6:
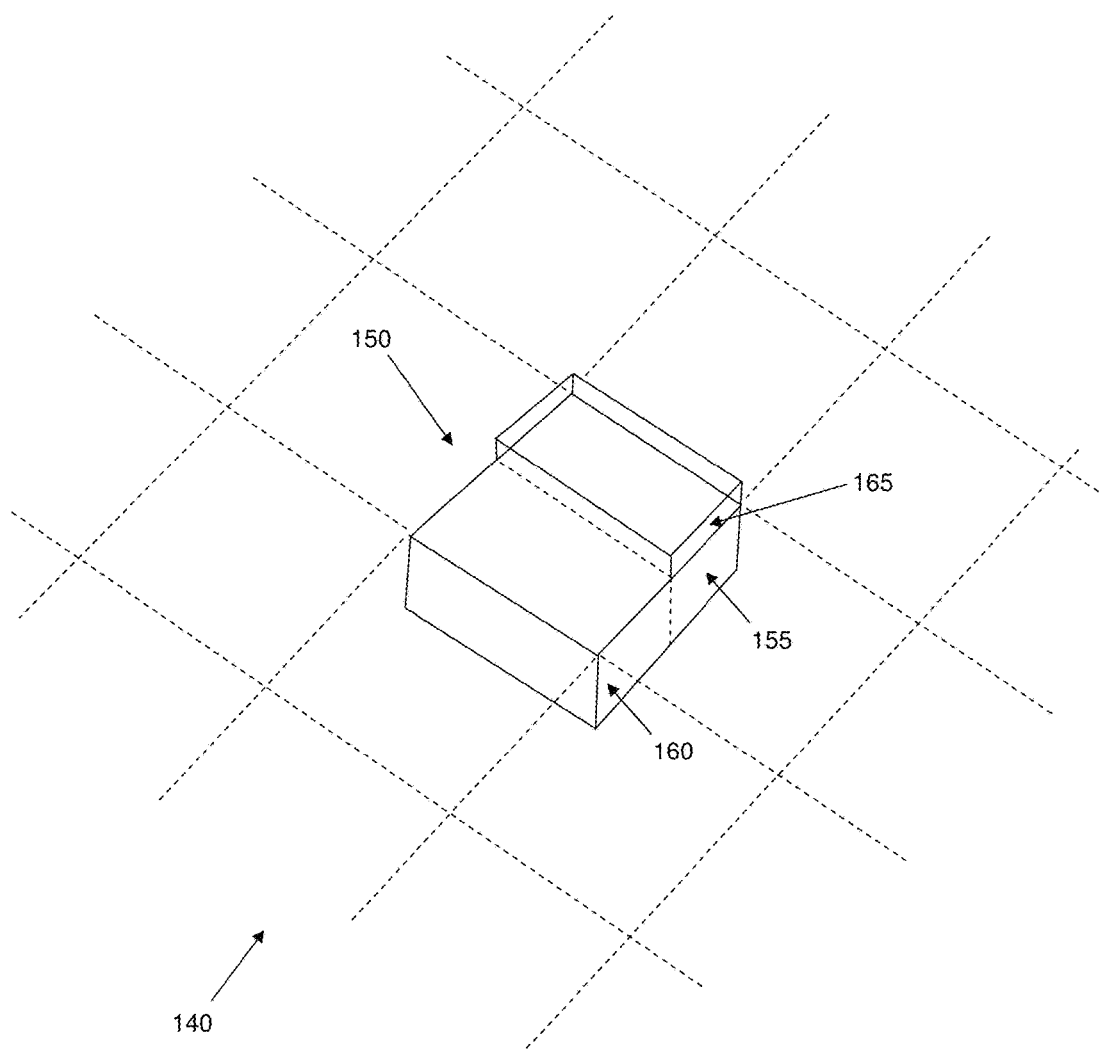
FIG. 6 is a schematic view of a single-filter detector which may be utilized in the X-ray detector assembly of the novel multi-energy (including dual energy) CT imaging system shown in FIG. 4.

More particularly, and looking now at FIG. 6, with the improved approach of the present invention, each detector 150 of X-ray detector assembly 140 is provided with two separate detection regions 155, 160. Detection region 155 is provided with a filter 165 which is configured to maximize the detection of higher energy photons (whereby to provide the "high energy measurement" used for dual energy CT scanning). Detection region 160 is not provided with a filter (hence, the detector shown in FIG. 6 may be considered to be a "single-filter detector", rather than a "dual-filter detector" such as is shown in FIG. 5).

As a result of this construction, detection region 155 will provide a measurement "X" which is representative of the higher energy portion of the X-ray spectrum passing through the object which is being scanned, and detection region 160 will provide a measurement "Y" which is representative of the total X-ray spectrum passing through the object which is being scanned. The present invention recognizes that if the value of the aforementioned measurement "X" is subtracted from the value of the aforementioned measurement "Y", the resulting value "Z" will be representative of the lower energy portion of the X-ray spectrum passing through the object which is being scanned. Thus, with this approach, by measuring the high energy photons passing through filter 165 and striking detection region 155 (i.e., the aforementioned measurement "X"), the "high energy measurement" used for dual energy CT scanning can be obtained. And by measuring the total X-ray spectrum striking detection region 160 (i.e., the aforementioned measurement "Y"), and then subtracting the value of the higher energy portion of the X-ray spectrum striking detection region 155 (i.e., the aforementioned measurement "X"), the "low energy measurement" (i.e., the aforementioned measurement "Z") can be obtained. In this way, the "single-filter detector" shown in FIG. 6 can be used to acquire the "high energy measurement" and the "low energy measurement" used for dual energy CT scanning.

Alternatively, a proxy for the "high energy measurement" can be taken as the signal striking region 160, as its average spectral response represents a higher energy than that of region 155, and the "low energy measurement" can be taken as the signal striking region 155, since filter 165 will ensure that those photons striking region 155 will be at a lower energy level than the photons striking region 160.

Method for Performing Multi-Energy (Including Dual Energy) Computed Tomography (CT) Imaging In accordance with the present invention, there is also provided a new process for using the measurements taken at two or more different polychromatic X-ray energies to provide multi-energy (including dual energy) CT imaging.

For clarity of description, multi-energy (including dual energy) CT imaging system 105 will generally hereinafter be discussed in the context of a dual energy CT imaging system, however, it should be appreciated that the CT imaging system may utilize three or more energy measurements without departing from the scope of the present invention.

The process described below shows how polychromatic dual energy data can be processed into synthetic monochromatic images which are both free of beam hardening artifacts and which contain information on material composition.

More particularly, when dual energy CT imaging is to be performed on an object (e.g., a body or a container), the object is placed in center opening 120 of novel dual energy CT imaging system 105, rotating disc 130 is rotated about fixed gantry 125, X-ray tube assembly 135 is energized so as to emit polychromic X-ray beam 145, and X-ray detector assembly 140 is operated so as to collect two energy measurements for each detector of X-ray detector assembly 140, i.e., a polychromatic "high energy measurement" and a polychromatic "low energy measurement".

As discussed above, and as shown in FIG. 5, the two energy measurements may be obtained for each detector by using a dual-filter detector where two different filters are positioned over each detector 150, i.e., by positioning filter 165 over detection region 155 and by positioning filter 170 over detection region 160. In this way, the "high energy measurement" is obtained from the output of detection region 155 and the "low energy measurement" is obtained from the output of detection region 160.

Alternatively, and more preferably, and as also discussed above, the two energy measurements may be obtained for each detector of X-ray detector assembly 140 by positioning a filter over half of the detector and leaving the other half of the detector exposed (i.e., by positioning filter 165 over detection region 155 and leaving detection region 160 unfiltered, in the manner shown in FIG. 6). In this way, the polychromatic "high energy measurement" may be obtained from the output of detection region 155 and a polychromatic "low energy measurement" may be obtained from the the output of detection region 160.

These two polychromatic energy measurements are made for each detector of X-ray detector assembly 140 for each rotational position of rotating disc 130 about fixed gantry 125, i.e., for each "line of response" of the X-ray beam passing through the object which is being scanned), thereby yielding two polyenergetic sinograms, $g_{HIGH}$ ("high energy") and $g_{LOW}$ ("low energy").

Figure 7:
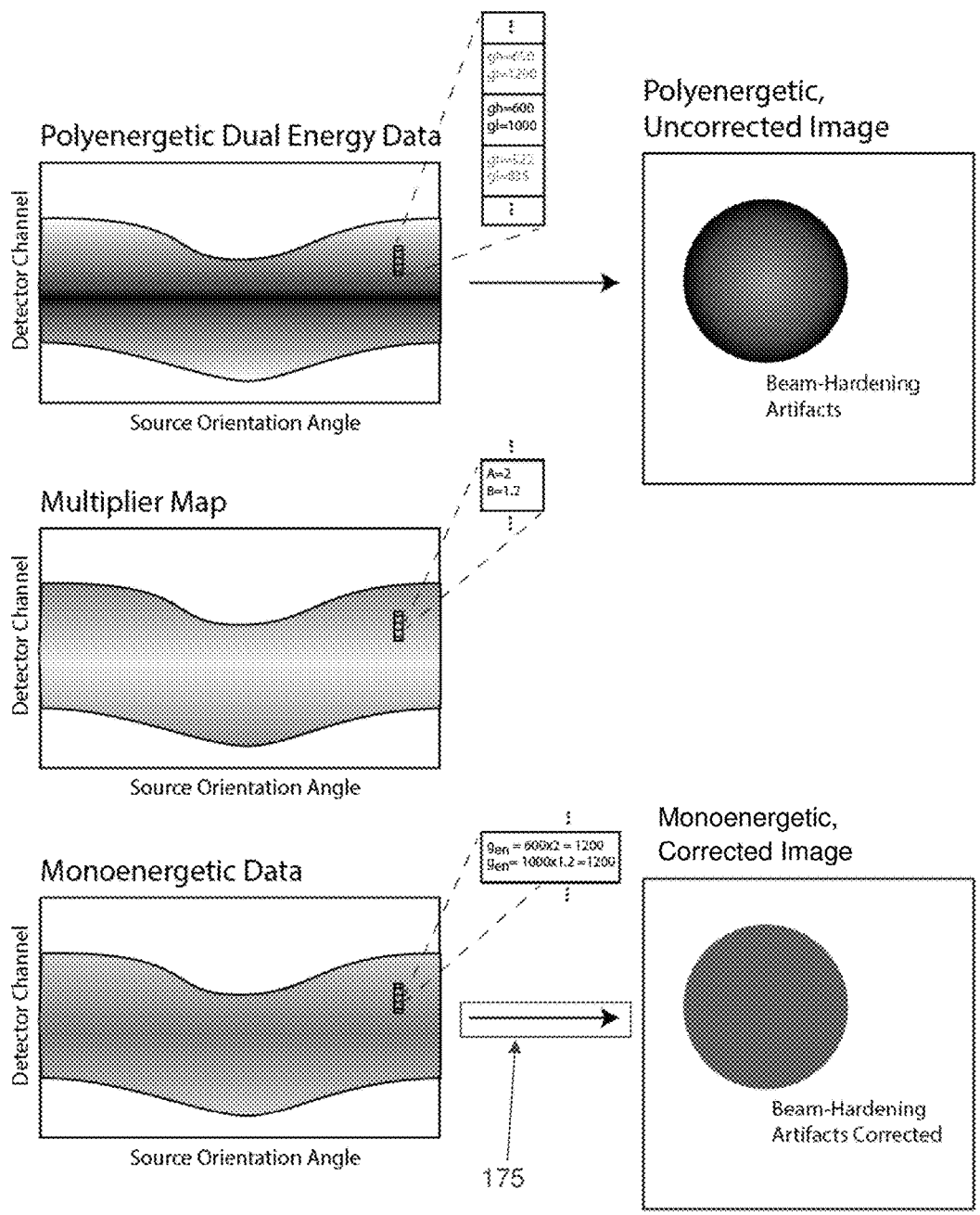
FIG. 7 is a schematic representation showing how polyenergetic data may be transformed to monoenergetic data.
Figure 8:
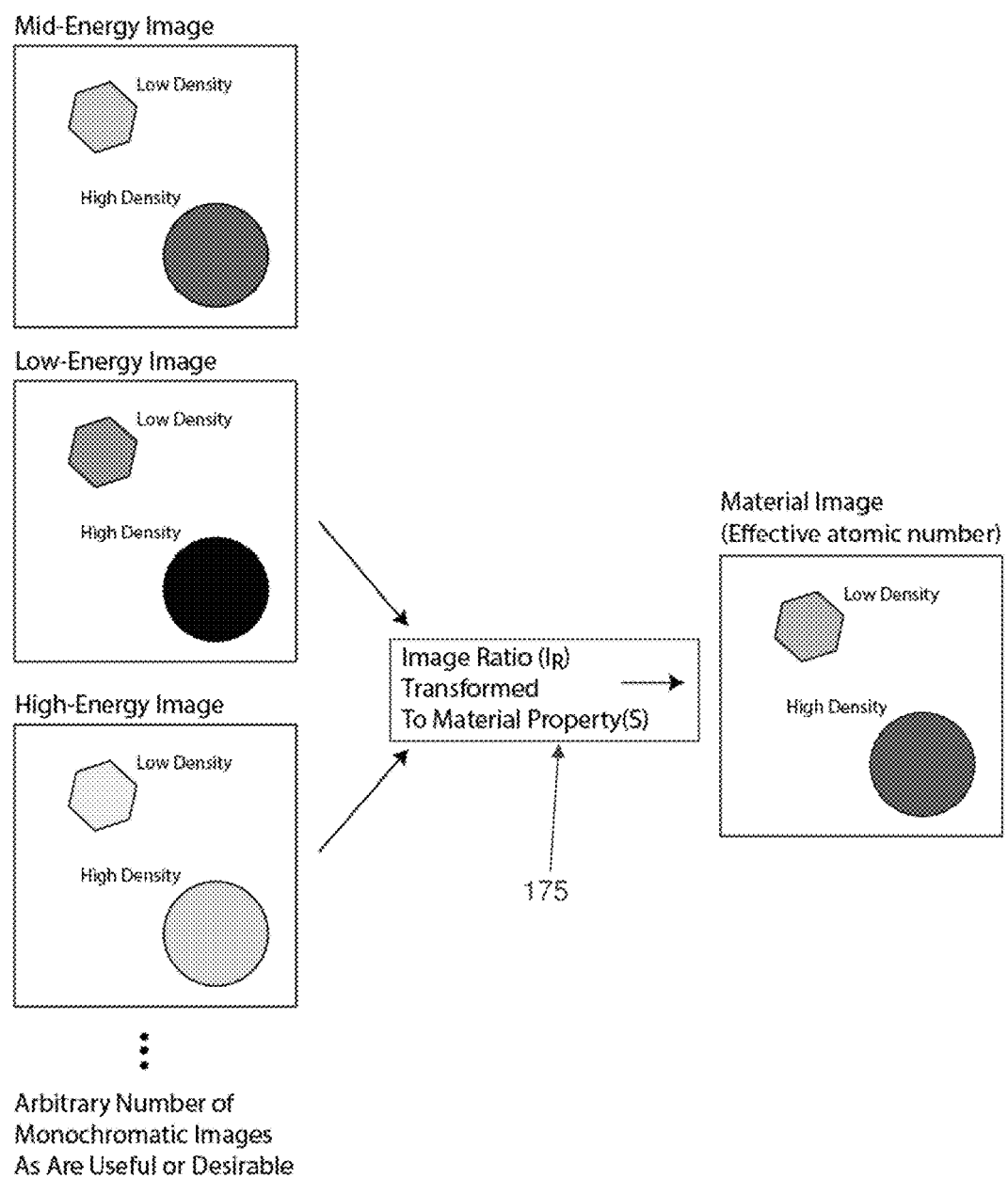
FIG. 8 is a schematic representation showing how multiple monoenergetic data sets and images may be produced, and multiple monoenergetic images may be transformed into an image conveying material properties.
Figure 9:
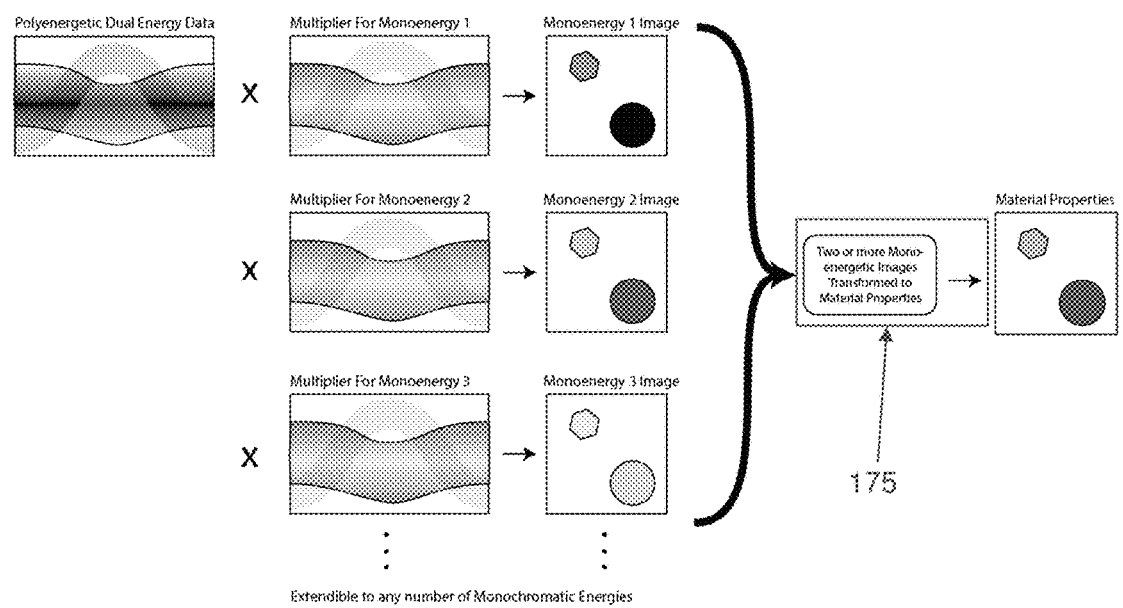
FIG. 9 is a schematic view showing how polyenergetic data sets may be transformed into any number of monoenergy data sets, and how two or more monoenergetic images may be transformed into an image conveying material properties.

Then, for each line of response, the ratio $g_{HIGH}/g_{LOW}$ (or "R") is computed, e.g., using a processor 175 (FIGS. 7-9).

The signal for any given line of response, whether associated with a filtered detector or an unfiltered detector (i.e., $g_{HIGH}$ or $g_{LOW}$, respectively), can be converted to the predicted signal for a purely monochromatic system of ANY monoenergy. This is achieved using a lookup table where R and g (either $g_{HIGH}$ or $g_{LOW}$) are used as the lookup indices to obtain the appropriate multiplier to transform the CT-acquired polyenergetic sinogram g (either $g_{HIGH}$ or $g_{LOW}$) into a synthetic monoenergetic sinogram $G_{ENERGY}$, where "$_{ENERGY}$" may be any monoenergetic level (e.g., $G_{160}$ which represents the synthetic monoenergetic sinogram at a monoenergy of 160 kev, $G_{40}$ which represents the synthetic monoenergetic sinogram at a monoenergy of 40 kev, etc.). In practice, because the response of the filtered and unfiltered channels are different, separate tables and separate lookup values are required for each of the filtered and unfiltered channels (i.e., the multipliers "$A_{ENERGY}$" and "$B_{ENERGY}$" respectively to produce a corresponding monochromatic sinogram of $G_{ENERGY}$). In this way, synthetic monoenergetic signal levels are predicted for every line of response, generating a full resolution monoenergetic synthetic sinogram. This may be done for any monoenergy using the appropriate multipliers.

Next, CT reconstruction techniques are applied to monoenergetic sinograms to produce monoenergetic images, i.e., $I_{ENERGY}$. The monoenergetic images may be produced for any monoenergy, e.g., $I_{160}$ which is the synthetic monoenergetic image at a monoenergy of 160 kev, $I_{40}$ which is the synthetic monoenergetic image at a monoenergy of 40 kev, etc. Any number of monoenergetic images can be generated from the data acquired using the methods described. These monoenergetic images are free of beam hardening artifacts and are therefore potentially useful for that reason alone. By way of example but not limitation, a single monoenergetic image could be potentially very useful for "radiation planning". In radiation therapy it is useful to know how the radiation used to target and kill tumors attenuates as the radiation beam travels through the body. A monoenergetic image can be generated at the same energy as the radiation used for therapy purposes. Each location within the image (i.e., each voxel) contains the predicted attenuation properties of the material for the therapy beam.

By way of example but not limitation, and looking now at FIG. 7, the top of the figure shows a representation of polychromatic dual energy data. In the field of tomographic imaging, raw data commonly takes on the form of a "sinogram" or "fanogram". The data on the left side of FIG. 7 are in sinogram format. Each "detector channel" consists of several filtered detectors. For example, with a dual energy system, there are two polyenergetic signals which are measured, $g_{HIGH}$ and $g_{LOW}$ (for high and low polyenergetic ranges, respectively). The insert shows example numerical data for several detector pairs. This raw data could be turned into an uncorrected polyenergetic image using any number of industry-standard reconstruction techniques including filtered back projection. The polyenergetic image would suffer from beam-hardening image artifacts. The middle row of FIG. 7 shows an example multiplier map which transforms the raw polyenergetic data into monoenergetic data. The multiplier for each detector channel has two components, A and B, to convert the polyenergetic signals $g_{HIGH}$ and $g_{LOW}$ respectively. The bottom row of FIG. 7 shows the resulting monoenergetic data. The two polyenergetic signals $g_{HIGH}$ and $g_{LOW}$ are converted to a monoenergetic signal $g_{ENERGY}$, where "$_{ENERGY}$" may be any monoenergetic level (e.g., $G_{160}$ which represents the synthetic monoenergetic sinogram at a monoenergy of 160 kev, $G_{40}$ which represents the synthetic monoenergetic sinogram at a monoenergy of 40 kev, etc.). Monoenergetic data does not suffer from beam hardening artifacts when turned into an image.

Synthetic monoenergetic images also contain information on the material composition along each line of response. For example, a mathematical function rho($I_{HIGH}$, $I_{LOW}$) could be used to directly determine the electron density of the material at that location (i.e., voxel).

From a computational efficiency point of view, the preferred embodiment uses a lookup table to transform the monoenergetic values at each location within the image into a material value (in this example, rho).

The underlying physical interactions which determine the attenuation of X-rays are generally characterized by Compton scattering (interacting with loosely-bound electrons) and the photoelectric effect (resonant interactions with electrons in atomic shells). Any physical property strongly dependent on the measured strength of these two kinds of interactions can be evaluated. For example, the mass-density of a material, largely dependent on the kind of atoms the material is composed of (a function of the photoelectric effect) and the number of atoms per volume (a function of the electron density), can be determined using the multiple synthetic monoenergetic images $I_{HIGH}$, $I_{LOW}$ (which could be, for example, $I_{160}$, $I_{40}$).

Looking now at FIG. 8, although any number of monoenergetic datasets and images can be made, in the preferred embodiment, three monochromatic images are made. The mid-energy image optimizes the signal/noise ratio and is free of beam-hardening artifacts. The low and high-energy monochromatic images are transformed to produce an image of the material atomic composition.

Generation of Lookup Tables for Monoenergetic Sinograms

The conversion between polyenergetic sinogram data into monoenergetic sinogram data has been described above as a mathematical function, with the preferred embodiment generalized to a lookup table. The mathematical function and/or lookup table contents could be determined entirely from theoretical computations or from empirical data. For both approaches, the goal is to transform the polyenergetic signals measured at the detectors to the expected monoenergetic signals. To verify that the transform operation produces the "expected" monoenergetic signals, it is usually convenient to select test objects of simple shape and composition. In most embodiments, the "expected" values are the best scientifically derived values. In our present embodiment, these target values are obtained from data published by the National Institute of Standards and Technology (NIST), but could be obtained from any source.

Using a completely theoretical approach, one would model the spectrum of the X-ray source, and compute the expected signal level for the different kinds of filtered detectors. The signal levels for the various filtered detectors would be computed a second time assuming a monoenergetic X-ray source. Taking the ratio of the computed detector signals for the monoenergetic X-ray source to the computed detector signals for the polyenergetic source would determine the multipliers necessary to transform a measured polyenergetic signal to the target monoenergy signal.

Using a completely empirical approach would involve making measurements of many objects (with varying composition and thickness) using a standard broad-spectrum (i.e., polychromatic) X-ray source. The equivalent measurements would be acquired using a monoenergetic source. By comparing values, one could determine the multiplicative values (e.g., "$A_{ENERGY}$" and "$B_{ENERGY}$") to translate one set of measurements (i.e., the polychromatic measurements) to another set of measurements (i.e., the monochromatic measurements at the monoenergetic energy level "ENERGY", e.g., 160 kev, 40 kev, etc.). However, it will be appreciated that a purely empirical approach is challenging because generating monochromatic X-rays is generally difficult, and because the number measurements would be large.

A practical approach, and the preferred embodiment for the present invention, involves a predominantly theoretical approach which is fine-tuned to match empirical measurements. Known material samples with varying thicknesses can be scanned using a polyenergetic X-ray source to generate polyenergetic data, and then the polyenergetic data can be transformed to corresponding monoenergetic data using the derived lookup tables. The monoenergetic detector response to these known samples are easily computed, and can be compared with the results using the lookup process. The table values can then be adjusted to produce the correct known response.

FIGS. 9 and 10 are schematic views showing how lookup tables may be used to generate multipliers for transforming polyenergetic data sets into any number of monoenergetic data sets, each one free of beam hardening. Monoenergetic images can then be transformed into a mapping of material properties such as effective atomic number or electron density.

Generation of Lookup Tables for Determining $Z_{effective}$ or Other Material Properties The conversion between monoenergetic sinogram data (i.e., $g_{ENERGY}$, which could be, for example, $g_{160}$, $g_{40}$, etc.) and monoenergetic image data (i.e., $I_{ENERGY}$, which could be, for example, $I_{160}$, $I_{40}$, etc.), and material properties, is a mathematical function. In the preferred embodiment, this function is reduced to a tabular form. The values within the table can be derived from the known physical properties of materials or from empirical analysis of data. In the preferred embodiment, the table is empirically derived. For example, samples of varying mean atomic number ($Z_{effective}$) are scanned. The ratio of two monoenergetic images (e.g., $I_{160}$, $I_{40}$) is used as an index into a table which returns the $Z_{effective}$ value. Thus, to generate the table values, the image ratio and $Z_{effective}$ value are recorded for a sample material. Data from six sample materials is collected and a best fit function $Z_{eff}$(Image Ratio) is determined.

Modifications

It will be appreciated that still further embodiments of the present invention will be apparent to those skilled in the art in view of the present disclosure. It is to be understood that the present invention is by no means limited to the particular constructions herein disclosed and/or shown in the drawings, but also comprises any modifications or equivalents within the scope of the invention.

What is claimed is:
1. A multi-energy computed tomography (CT) imaging system for providing an image of an object, the multi-energy computed tomography (CT) imaging system comprising:
   a polychromatic X-ray source;
   a detector for detecting X-rays from the polychromatic X-ray source after the X-rays have passed through an object and for providing a first set of polychromatic energy measurements relating to a first polychromatic X-ray spectrum passed through the object and for providing a second set of polychromatic energy mea- surements relating to a second polychromatic X-ray spectrum passed through the object; and a processor configured to:
(i) transform the first set of polychromatic energy measurements into a corresponding first monochromatic data set associated with X-rays at a selected first monochromatic energy level, and to transform the second set of polychromatic energy measurements into a corresponding second monochromatic data set associated with X-rays at a selected second monochromatic energy level;
(ii) transform the first monochromatic data set into a first monochromatic image and transform the second monochromatic data set into a second monochromatic image; and
(iii) use at least one of the first monochromatic image and the second monochromatic image to perform at least one of (a) provide an image free from beam hardening artifacts, and (b) provide identification of material properties within the object.

2. The multi-energy computed tomography (CT) imaging system according to claim 1, wherein the detector comprises a first section and a second section, wherein the multi-energy computed tomography (CT) imaging system further comprises a first filter and a second filter, and further wherein the first set of polychromatic energy measurements is provided by positioning the first filter between the polychromatic X-ray source and the first section of the detector, and the second set of polychromatic energy measurements is provided by positioning the second filter between the polychromatic X-ray source and the second section of the detector.

3. The multi-energy computed tomography (CT) imaging system according to claim 2, wherein at least one of the first filter and the second filter is disposed between the polychromatic X-ray source and the object.

4. The multi-energy computed tomography (CT) imaging system according to claim 2, wherein at least one of the first filter and the second filter is disposed between the object and the detector.

5. The multi-energy computed tomography (CT) imaging system according to claim 2, wherein the first filter is disposed between the object and the detector.

6. The multi-energy computed tomography (CT) imaging system according to claim 1, wherein the detector comprises a first section and a second section, wherein the multi-energy computed tomography (CT) imaging system further comprises a first filter, and further wherein the first set of polychromatic energy measurements is provided by positioning the first filter between the polychromatic X-ray source and the first section of the detector, and the second set of polychromatic energy measurements is provided by calculating a difference between an output of the first section of the detector and an output of the second section of the detector.

7. The multi-energy computed tomography (CT) imaging system according to claim 6, wherein the first filter is disposed between the polychromatic X-ray source and the object.

8. The multi-energy computed tomography (CT) imaging system according to claim 1, wherein the corresponding first monochromatic data set comprises a first sinogram, and wherein the corresponding second monochromatic data set comprises a second sinogram.

9. The multi-energy computed tomography (CT) imaging system according to claim 1, wherein the multi-energy computed tomography (CT) imaging system further comprises a lookup table, and further wherein the lookup table is used to transform at least one of the first set of polychromatic energy measurements into a corresponding first monochromatic data set and the second set of polychromatic energy measurements into a corresponding second monochromatic data set.

10. The multi-energy computed tomography (CT) imaging system according to claim 9, wherein the lookup table provides at least one multiplier for converting at least one of the first set of polychromatic energy measurements into the corresponding first monochromatic data set and the second set of polychromatic energy measurements into the corresponding second monochromatic data set.

11. The multi-energy computed tomography (CT) imaging system according to claim 9, wherein indices of the lookup table comprise:
(i) at least one of the first set of polychromatic energy measurements and the second set of polychromatic energy measurements; and
(ii) a function which is sensitive to differences between the first set of polychromatic energy measurements and the second set of polychromatic energy measurements.

12. The multi-energy computed tomography (CT) imaging system according to claim 9, wherein indices of the lookup table comprise:
(i) at least one of the first set of polychromatic energy measurements and the second set of polychromatic energy measurements; and
(ii) a ratio between the first set of polychromatic energy measurements and the second set of polychromatic energy measurements.

13. The multi-energy computed tomography (CT) imaging system according to claim 1, wherein the processor generates an image free from beam hardening artifacts by presenting one of the first monochromatic image and the second monochromatic image.

14. The multi-energy computed tomography (CT) imaging system according to claim 1, wherein the processor generates an image free from beam hardening artifacts by presenting a composite image of the first monochromatic image and the second monochromatic image.

15. The multi-energy computed tomography (CT) imaging system according to claim 14, wherein the composite image is a weighted composite image.

16. The multi-energy computed tomography (CT) imaging system according to claim 14, wherein the composite image of the first monochromatic image and the second monochromatic image comprises a plurality of voxels, and further wherein each voxel of the composite image comprises a voxel selected from the first monochromatic image or the second monochromatic image.

17. The multi-energy computed tomography (CT) imaging system according to claim 1, wherein the processor uses at least one of the first monochromatic image and the second monochromatic image to provide identification of materials within the object by generating an image whose voxel values reflect material properties of the scanned object.

18. The multi-energy computed tomography (CT) imaging system according to claim 1, wherein the processor uses at least one of the first monochromatic image and the second monochromatic image to provide identification of materials within the object by generating an image whose voxel values reflect an electron density (rho value) of the scanned object.

19. The multi-energy computed tomography (CT) imaging system according to claim 1, wherein the processor uses at least one of the first monochromatic image and the second monochromatic image to provide identification of materials within the object by generating an image whose voxel values reflect $Z_{effective}$ of the scanned object.

20. The multi-energy computed tomography (CT) imaging system according to claim 1, wherein the detector provides a third set of polychromatic energy measurements relating to a third polychromatic X-ray spectrum passed through the object.

21. A multi-energy computed tomography (CT) imaging method for providing an image of an object free from beam hardening artifacts and/or providing identification of material properties of the object, the multi-energy computed tomography (CT) imaging method comprising:

providing a first set of polychromatic energy measurements relating to a first polychromatic X-ray spectrum passed through the object and providing a second set of polychromatic energy measurements relating to a second polychromatic X-ray spectrum passed through the object;

transforming the first set of polychromatic energy measurements into a corresponding first monochromatic data set associated with X-rays at a selected first monochromatic energy level, and transforming the second set of polychromatic energy measurements into a corresponding second monochromatic data set associated with X-rays at a selected second monochromatic energy level;

transforming the first monochromatic data set into a first monochromatic image, and transforming the second monochromatic data set into a second monochromatic image; and using at least one of the first monochromatic image and the second monochromatic image to provide at least one of (a) an image free from beam hardening artifacts, and (b) identification of material properties within the object.

* * * * *